(12) United States Patent
Teles et al.

(10) Patent No.: US 6,211,416 B1
(45) Date of Patent: Apr. 3, 2001

(54) METHOD FOR PRODUCING ENOL ETHERS (75) Inventors: Joaquim Henrique Teles, Altrip; Norbert Rieber, Mannheim; Klaus Breuer, Altrip; Dirk Demuth, Mannheim; Hartmut Hibst, Schriesheim; Heinz Etzrodt, Neustadt; Udo Rheude, Otterstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/424,855

(22) Filed: Dec. 6, 1999

(30) Foreign Application Priority Data

Jun. 23, 1997 (DE) .............................. 197 26 667

(51) Int. Cl.$^7$ .................................. C07C 41/28
(52) U.S. Cl. .................... 568/691; 568/591; 568/630; 568/631; 568/640; 568/657; 568/664; 502/232; 502/253
(58) Field of Search ..................... 568/691, 579, 568/630, 631, 640, 657, 664; 502/232, 253

(56) References Cited

U.S. PATENT DOCUMENTS

| | | | |
|---|---|---|---|
| 4,891,451 | * 1/1990 | Hoelderich et al. | 568/691 |
| 4,960,954 | * 10/1990 | Hoelderich et al. | 568/691 |
| 5,767,325 | * 6/1998 | Schroder et al. | 568/691 |
| 6,060,035 | * 5/2000 | Teles et al. | 423/326 |
| 6,087,538 | * 7/2000 | Teles et al. | 568/591 |

\* cited by examiner

Primary Examiner—Rosalynd Keys
(74) Attorney, Agent, or Firm—Oblon, Spivak, McClelland, Maier & Neustadt, P.C.

(57) ABSTRACT

Enol ethers of the formula I

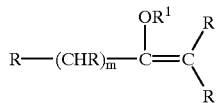

where $R^1$ is an aliphatic, cycloaliphatic, araliphatic, aromatic or heterocyclic radical which may carry further substituents which do not react with acetylenes or allenes, and the radicals R, independently of one another, are hydrogen or aliphatic, cycloaliphatic, araliphatic, aromatic or heterocyclic radicals, which may be bonded to one another to form a ring, and m is 0 or 1, are prepared by reacting an acetal or ketal of the formula II

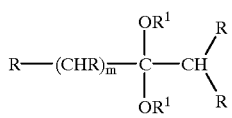

with an acetylene or allene of the formula III or IV

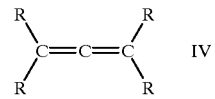

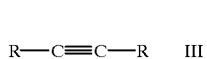

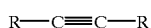

where R and $R^1$ have the abovementioned meanings, in the gas phase at elevated temperatures in the presence of a zinc- or cadmium- and silicon- and oxygen-containing heterogeneous catalyst.

8 Claims, 2 Drawing Sheets

*FIG. 1*

FIG. 2

METHOD FOR PRODUCING ENOL ETHERS

The present invention relates to a process for the preparation of enol ethers by comproportionation of ketals or acetals with alkynes or allenes in the gas phase in the presence of a zinc- or cadmium- and silicon- and oxygen-containing heterogeneous catalyst.

It is known that ketals or acetals can be converted into the corresponding enol ethers, either in the liquid phase with acidic catalysts (according to EP 703 211 or EP 490 221) or in the gas phase over heterogeneous catalysts (according to DE 19544450) with elimination of alcohol, according to the following equation:

The enol ethers thus obtained are important starting compounds of the preparation of pharmaceutical products and fragrances.

The stated known processes permit the preparation of the enol ethers in good yields in some cases but have the following disadvantages:

The reaction in the liquid phase according to EP 703 211 requires the use of a dissolved foreign substance, namely an organic acid, the removal of which from the reaction mixture necessitates an additional separation step, and the process according to EP 490 221 is applicable only to acetals. Compared with the processes in the liquid phase using homologously dissolved catalyst, the process according to DE 19544450 has the advantage of the reaction in the gas phase over a heterogeneous catalyst but requires rather high temperatures.

Common to all these processes is the fact that one mole of alcohol is liberated per mole of ketal or acetal and has to be separated off with additional and in some cases considerable purification costs and as a rule discarded. This applies in particular to methanol, which frequently forms azeotropic mixtures. The weight yield, based on ketal or acetal, is thus inevitably reduced.

It is an object of the present invention to provide a process which can be carried out continuously over a heterogeneous catalyst with good yields and is applicable both to ketals and to acetals and in which the alcohol originating from the ketal or acetal is not obtained as an associated product in stoichiometric amounts.

We have found that this object is achieved, according to the invention, by a process for the preparation of enol ethers of the formula I where $R^1$ is an aliphatic, cycloaliphatic, araliphatic, aromatic or heterocyclic radical which may carry further substituents which do not react with acetylenes or allenes, and the radicals R, independently of one another, are hydrogen or aliphatic, cycloaliphatic, araliphatic, aromatic or heterocyclic radicals, which may be bonded to one another to form a ring, and m is 0 or 1, wherein an acetal or ketal of the formula II is reacted with an acetylene or allene of the formula III or IV where R and $R^1$ have the abovementioned meanings, in the gas phase in the presence of a zinc- or cadmium- and silicon- and oxygen-containing heterogeneous catalyst.

Although the mechanism of the novel reaction is not known in detail, the reaction may be formally considered as if one mole of an alcohol $R^1OH$ from the dialkoxy compound of the formula II is transferred to the acetylene or allene with formation of the enol ether of the formula I.

The ketals or acetals of the formula II which are to be used as starting materials are disclosed in the literature, for example in U.S. Pat. No. 2,667,517 and EP-A-0197283, the two radicals $R^1$ generally being identical.

R is preferably alkyl, in particular of 1 to 6 carbon atoms, or hydrogen and $R^1$ is an alkyl in particular of 1 to 8 carbon atoms.

Particularly suitable acetals are open-chain compounds. Examples of such acetals are dimethyl acetals, diethyl acetals, di-n-propyl acetals, di-n-butyl acetals, diisobutyl acetals, di-n-pentyl acetals, diisopentyl acetals, di-n-hexyl acetals and diisohexyl acetals of aldehydes of the formula where R has the abovementioned meanings.

Examples of such acetals are:

Acetaldehyde dimethyl acetal, acetaldehyde diethyl acetal, acetaldehyde dipropyl acetal, propionaldehyde dimethyl acetal, propionaldehyde diethyl acetal, propionaldehyde dipropyl acetal, propionaldehyde dibutyl acetal, butyraldehyde dimethyl acetal, butyraldehyde diethyl acetal, butyraldehyde dipropyl acetal, butyraldehyde dibutyl acetal, butyraldehyde dipentyl acetal, valeraldehyde dimethyl acetal, valeraldehyde diethyl acetal, valeraldehyde dipropyl acetal, valeraldehyde dibutyl acetal, valeraldehyde dipentyl acetal, isovaleraldehyde dimethyl acetal, isovaleraldehyde diethyl acetal, isovaleraldehyde dipropyl acetal, isovaleraldehyde dibutyl acetal, isovaleraldehyde dipentyl acetal, hexanal dimethyl acetal, hexanal diethyl acetal, hexanal dipropyl acetal, hexanal dibutyl acetal, hexanal dipentyl acetal, hexanal dihexyl acetal, 2-ethylhexanal dimethyl acetal, 2-ethylhexanal diethyl acetal, 2-ethylhexanal dipropyl acetal, 2-ethylhexanal dibutyl acetal, 2-ethylhexanal dipentyl acetal, 2-ethylhexanal dihexyl acetal and nonanal dimethyl acetal.

Examples of suitable ketals are:

Dimethyl, diethyl, di-n-propyl, di-n-butyl, diisobutyl ketals of acetone, of 2-butanone, of 2- or 3-pentanone, of 2- or 3-hexanone, of cyclopentanone or of cyclohexanone. A particularly preferred starting material is 2,2-dimethoxypropane (acetone dimethyl ketal).

Although any desired acetylenes or allenes may be chosen as starting materials, technically readily obtainable acetylenes and/or allenes of 2 or 3 to 8, preferably 3 to 8, carbon atoms, in particular methylacetylene or allene or mixtures thereof, for example as can be isolated from a $C_3$ stream of a steam cracker, are preferably used. In general, the ketals or acetals are preferably reacted with acetylenes or allenes to give a uniform enol ether I. This means, for example, that, in the formula II, a compound in which m is 1 corresponds to an allene having the same radicals R and a compound in which m is 0 corresponds to an acetylene having the same radicals R.

The reaction of the ketals or acetals with the acetylenes or allenes is carried out in the presence of the heterogeneous zinc- or cadmium- and silicon- and oxygen-containing catalyst in the gas phase, either over a fixed bed or in a fluidized bed at from 50 to 400° C., preferably from 100 to 250° C., particularly preferably from 120 to 200° C. and at from 0.1 to 50, in particular from 0.8 to 20, particularly preferably from 0.9 to 10, bar (all pressures are based on the sum of the partial pressures of the starting materials).

If required, for reasons of operational safety and for better heat removal, the reaction mixture can be diluted with inert gas, such as nitrogen, argon, low molecular weight alkanes or olefins.

The molar ratio of ketal or acetal to alkyne or allene may be from 0.01 to 100, preferably from 0.1 to 2, particularly preferably from 0.7 to 1.3.

Suitable zinc- or cadmium- and silicon- and oxygen-containing catalysts are cadmium silicates and preferably zinc silicates, for example silicates selected from the group consisting of (a) X-ray amorphous zinc silicate or cadmium silicate, prepared by impregnating a silica carrier with a zinc or cadmium salt, (b) crystalline zinc silicate having essentially the composition and structure of the hemimorphite of the formula $Zn_4Si_2O_7(OH)_2 \cdot H_2O$, where the zinc may be present in an amount up to 25% below or above the stoichiometric amount, based on the stoichiometric composition, and/or (c) essentially X-ray amorphous zinc silicate, prepared by precipitation in aqueous solution of a soluble silicon and zinc compound, of the formula V $$Zn_aSi_cO_{-2c-0.5e}(OH)_e \cdot f\ H_2O \qquad V,$$

where e is from 0 to 2a+4c, the ratio a/c is from 1 to 3.5 and the ratio f/a is from 0 to 200.

(a) X-ray amorphous zinc silicate or cadmium silicate catalysts are obtained, for example, by loading amorphous silica with a zinc salt or cadmium salt and forming the catalyst by a thermal treatment.

The $SiO_2$ carrier is at least predominantly amorphous, has a BET surface area of from 10 to 1500, particularly preferably from 100 to 500, m²/g and a water absorptivity of from 0.1 to 2, particularly preferably from 0.7 to 1.3, ml/g and can be used in the form of powder or prepared moldings. The carrier may also be calcined prior to impregnation. However, the carrier is preferably not calcined.

The zinc or cadmium compound used is a compound soluble in a suitable solvent. Zinc(II) salts which are soluble in water or aqueous ammonia or alcohols, preferably lower alcohols, and whose decomposition temperature is below from 400° C. to 500° C. are preferably used.

An ammoniacal zinc(II) acetate solution is particularly preferably used for the impregnation. In some cases, it has proven advantageous to carry out the loading of zinc in a plurality of successive impregnation steps.

If the carrier is used in the form of a powder, the catalyst can be brought into the desired form by shaping (for example by mixing, kneading and extruding or pelleting).

To increase the pore volume, pore formers (for example superabsorbers such as Lutexal® P (from BASF Ludwigshafen) or Walocel® (methylcellulose/synthetic resin combination, from Wolff, Walsrode)) may also be added during the shaping.

Alternatively, another carrier, eg. $Al_2O_3$, may also be impregnated with a silica precursor compound (eg. $Si(OR)_4$) and with a zinc salt or cadmium salt.

The zinc or cadmium loading can be varied within wide limits. Typical values for an uncalcined precatalyst prepared by impregnating an $SiO_2$ carrier with a zinc salt or cadmium salt, are, for example, from 1 to 60, preferably from 7 to 30%, by weight of Zn or Cd. Contents of from 10 to 25% by weight (calculated in each case as ZnO or CdO) are particularly preferred. The precatalyst may furthermore be doped with other elements, preferably with alkali metals, alkaline earth metals or transition metals. Moreover, the catalytically active component may also be doped with up to 80, preferably up to 50, in particular up to 20, mol % of further metals, selected from the group (A) consisting of beryllium, magnesium, calcium, strontium, barium, manganese, iron, cobalt, nickel and copper and from the group (B) consisting of titanium, zirconium, hafnium, germanium, tin and lead, the elements of group (A) partially replacing zinc or cadmium and the elements of group (B) partially replacing silicon.

The precatalyst can then be calcined at up to 600° C., in particular from 80 to 300° C., in air or under an inert gas. Calcination at from 120 to 250° C. in air is particularly preferred.

After the preparation of the precatalyst, which is generally still catalytically inactive, by application of a zinc or cadmium compound to a silica carrier, it is preferable to carry out forming in which the actual active phase is formed in particular on the surface of the catalyst. This solid-state reaction is promoted by the presence of water, alcohols, preferably lower alcohols, or carboxylic acids, preferably lower carboxylic acids, and is therefore advantageously carried out by heating the precatalyst at from 50 to 400° C. in a water- or alcohol-containing atmosphere. The reaction is preferably carried out at from 100 to 250° C. in a water- or methanol-containing gas mixture. The reaction is particularly preferably carried out at from 120 to 200° C. using a methanol-containing gas mixture directly in the reactor in which the reaction with the alkyne or allene is subsequently to take place. If a precatalyst based on zinc acetate is used as the starting material, it is very easy to determine when the solid-state reaction is complete, since virtually no methyl acetate is to be found in the exit gas at this time. In some cases, it has proven advantageous to treat the precatalyst, for the formation of the active phase, under reaction conditions with a mixture of methanol with propyne and allene and possibly also other components (eg. propene or propane). The formation of the active layer is indicated by the increase in the propyne and allene conversion (after from about 5 to 30 minutes, depending on the temperature), by the increase in the selectivity (after 10 to 300 minutes, depending on the temperature) and by the decline in the concentration of methyl acetate in the exit gas. A steady state (with high propyne or allene conversions) and a high selectivity are achieved after from about 2 to 20 hours, depending on the temperature.

It is also possible to prepare the corresponding mercury silicates, which however are less suitable technically and ecologically.

Standard methods were used for characterizing the catalyst samples (fresh samples as well as samples removed from the reactor). The measured BET surface area, which is typically from 10 to 800 $m^2/g$, and the hardness are stated in the respective example. Catalysts having BET surface areas of from 100 to 400 $m^2/g$ are preferred. Furthermore, the samples were thoroughly investigated by means of powder X-ray diffractometry (XRD) and transmission electron microscopy (TEM). Neither of the structure analysis methods indicates any long-range order in the sense of a crystalline structure, all samples being amorphous. The distribution of the zinc over the carrier was investigated on appropriate sections under the electron microscope and by means of a microprobe. Even after removal from the reactor, all samples show that the catalyst has a substantially homogeneous elemental distribution and contains little or no crystalline ZnO. In the IR investigation (KBr pellet), the active catalyst prepared using zinc acetate shows no acetate bands (these are still visible in the case of the precatalyst at 1570, 1410, 670 and 610 $cm^{-1}$). In the $^{13}C$-CP-MAS-NMR, acetate signals are no longer present. In the $^{29}Si$-CP-MAS-NMR, the catalyst shows only the broad band at $-109$ ppm typical of amorphous $SiO_2$ and a shoulder at $-99$ ppm (about 10% of the intensity of the main peak). The elemental analysis of a zinc acetate/$SiO_2$ precatalyst shows that the molar C/Zn ratio is dependent on the calcination temperature. Catalysts dried at room temperature have a C/Zn ratio of 3.5–4. After the calcination at 200–250° C. (optimum temperature), the C/Zn ratio is from 1 to 2. At higher temperatures, the C/Zn ratio decreases even further, as does the catalytic activity of the catalysts formed therefrom. After calcination at 500° C. (24 hours), the C/Zn ratio in the precatalyst is 0.02. No active catalyst can be formed therefrom. Since the decomposition of the zinc acetate on the precatalyst is relatively slow, said precatalyst can even be exposed to higher temperatures for short times without the catalytic activity being completely lost.

(b) Hemimorphite as catalyst

Hemimorphite is a zinc silicate of the formula $Zn_4Si_2O_7(OH)_2.H_2O$. However, not only pure hemimorphite but in general heterogeneous catalysts which contain, as active component, at least predominantly zinc silicate having the structure of hemimorphite of the formula $Zn_4Si_2O_7(OH)_{2-y}O_y.x\ H_2O$, where x and y are each from 0 to 1, are suitable for the novel reaction.

The preparation of hemimorphite is disclosed in the literature. It may be carried out under standard conditions or hydrothermal conditions.

(b1) Preparation under standard conditions

A. G. Merkulov and B. S. Khristoforov, (Tr. Soveshch, Eksp. Tekh. Mineral. Petrogr., $8^{th}$ (1971), Meeting Date 1968, 322-8; Editor(s): V. V. Lapin; Publisher: "Nauka", Moscow, USSR) describe the preparation of various zinc silicates by a reaction of various zinc salts (carbonate, sulfate, chloride, acetate or oxide) with sodium silicate and sodium hydroxide in aqueous solution at 90–100° C. and at atmospheric pressure. Various zinc silicates are formed, depending on the pH established. Thus, pure sauconite having the composition $Zn_3Si_4O_{10}(OH)_2.n\ H_2O$ is formed at a final pH of 5–6. Pure willemite ($\alpha$-$Zn_2SiO_4$) is obtained at a pH of 6.5–8.5. On the other hand, pure hemimorphite ($Zn_4Si_2O_7(OH)_2.H_2O$) crystallizes out only in a weakly alkaline medium at a pH greater than 10.

Another paper by the stated authors (A. G. Merkulov and B. S. Khristoforov, Izv. Sib. Otd. Akad. Nauk SSSR, Ser. Khim. Nauk (1969), (4), 70–4) indicates that pure hemimorphite is formed in the reaction of zinc salts with sodium silicate and sodium hydroxide at 90–100° C. and atmospheric pressure in aqueous solution only at a pH of 10–12.

Furthermore, T. Baird, A. G. Cairns Smith and D. S. Snell (Reactivity of Solids, Proc. Int. Symp., 8th (1977), Göteborg, Meeting Date 1976, 337–42; Editor(s): J. Wood, O. Lindqvist and C. Helgesson; Publisher: Plenum Press, New York, N.Y.) were able to prepare large crystals of hemimorphite by reacting $Zn(OH)_2$ with silica and LiOH in aqueous solution at a pH of 10.

Finally, H. Nagata, M. Matsunage and K. Hosokawa (zairyo-to-Kankyo (1993) 42, 225–233) prepared hemimorphite by reacting aqueous zinc-sulfate solution with sodium hydroxide and aqueous sodium silicate solution at a pH of 13, separating off the precipitate obtained, washing it thoroughly and aging it at 85° C. for at least 24 hours.

(b2) Hydrothermal preparation

According to EP 165,647 hemimorphite can be prepared from an acid-treated clay mineral and zinc oxide or zinc hydroxide under hydrothermal conditions (170° C., 5 h). However, the pretreatment of the clay with acid is very expensive and this process is therefore disadvantageous.

According to D. M. Roy and F. A. Mumpton (Econ. Geol. (1956) 51, 432–443), hemimorphite can furthermore be obtained by hydrothermal reaction of mixtures of ZnO and $SiO_2$ at 175–200° C. (composition: 3 $ZnO+2SiO_2$). The product obtained contains predominantly hemimorphite but is contaminated with sauconite ($Zn_3Si_4O_{10}(OH)_2.4\ H_2O$).

Finally, P. Taylor and D. G. Owen, (Polyhedron (1984) 3(2) 151–155) describe the hydrothermal synthesis of hemimorphite by reacting ZnO with $SiO_2$ in aqueous solution at 150° C. However, long reaction times of at least 4 days were required for preparing products having a high hemimorphite content.

Although hemimorphite products obtained by the known methods described above are very suitable as catalysts for the novel addition reaction, it was found to be desirable to improve their properties further and to provide a preparation method which permits the preparation of catalysts having a reproducibly good property profile.

Accordingly, a novel preparation method, both under atmospheric pressure and under hydrothermal conditions, is proposed, in which an alkali metal or alkaline earth metal silicate, preferably sodium silicate, is reacted with a zinc salt, in particular zinc nitrate, and a base, such as an alkali metal or alkaline earth metal hydroxide, in particular sodium hydroxide, in aqueous solution at a pH of from 4 to 9.5, preferably from 5.5 to 8, in particular at around the neutral point, for example at a pH of from 6 to 7.5, at from 50 to 100° C., in particular from 70 to 100° C., in the case of atmospheric pressure and from 100 to 250° C., preferably from 100 to 200° C., in the case of hydrothermal conditions.

Pure hemimorphite having a Zn/Si ratio of 2 can be synthesized by this preparation method. However, hemimorphite preparations containing up to 25% less than or more than the stoichiometric amount of zinc, corresponding to an atomic Zn:Si ratio of from 1.6 to 2.5, are also obtained. Hemimorphites which contain a zinc excess of from 0 to 20% are preferred as catalysts. Hemimorphites which contain a zinc excess of from 0 to 10% are particularly preferred.

The hemimorphite products are obtained in the synthesis as white crystalline precipitate in the form of an aqueous suspension and must be separated from the aqueous solution by suitable measures, for example filtration or centrifuging. In the case of filtration, the filter cake obtained is then washed thoroughly sodium- and nitrate-free and then dried. The drying can be carried out at up to 600° C., the preferred temperature range being from 90 to 250° C. Thermogravimetric analyses have shown that the crystallized hemimorphite having the composition $Zn_4Si_2O_7(OH)_2.H_2O$ loses increasing proportions of its water of crystallization at from about 100 to 200° C. with retention of the hemimorphite structure, resulting in hemimorphite preparations having the composition $Zn_4Si_2O_7(OH)_2.x\ H_2O$ where x is less than 1 and decreases with increasing temperature. If drying is carried out in a higher temperature range from about 200 to 600° C., the $OH^-$ ions present in the hemimorphite are additionally converted into $O^{2-}$ ions and eliminated $H_2O(2\ OH^- \rightarrow H_2O+O^{2-})$, likewise with retention of the hemimorphite structure, resulting in hemimorphite preparations having the composition $Zn_4Si_2O_7(OH)_{2-2y}O_y.x\ H_2O$ where y is from 0 to 1 and increases with increasing temperature.

The hemimorphite preparations obtained after drying at up to 600° C., preferably from 90 to 450° C., and having the composition $Zn_4Si_2O_7(OH)_{2-2y}O_y.x\ H_2O$, where x and y are each from 0 to 1, are then usually processed to give catalytic moldings by the conventional shaping methods, for example pelleting or extrusion, or conversion into coated catalysts on steatite beads. Details are described in the examples.

Standard methods were used for characterizing the catalyst samples (fresh samples as well as samples removed from the reactor). The measured BET surface area is as a rule from 3 to 400 $m^2/g$. Catalysts having BET surface areas of from 20 to 300 $m^2/g$ are preferably used. Furthermore, the samples obtained by the novel preparation process were thoroughly investigated by means of powder X-ray diffractometry (XRD) and transmission electron microscopy (TEM). The measured powder X-ray diffraction pattern is in agreement with index card 5-0555 of the JCPDS-ICDD index (1995).

(c) X-ray amorphous zinc-silicate catalyst

It has now been found that an X-ray amorphous product having improved catalytic properties is obtained essentially under the same preparation conditions but in a shorter reaction time than the intermediate for the preparation of a crystalline hemimorphite.

According to the invention, for example, an aqueous suspension of an alkali metal or alkaline earth metal silicate is, for this purpose, reacted with an aqueous solution of a zinc salt at a) from 20° C., preferably 50° C., to the boiling point of the resulting aqueous suspension at b) a pH of from 4 to 9.5, preferably at a pH close to the neutral point, c) and at ratios of alkali metal silicate to zinc salt such that the conditions of the formula VI are fulfilled, and d) a residence time is maintained such that crystallization of the zinc silicate does not yet occur to any considerable extent.

Figure 2:
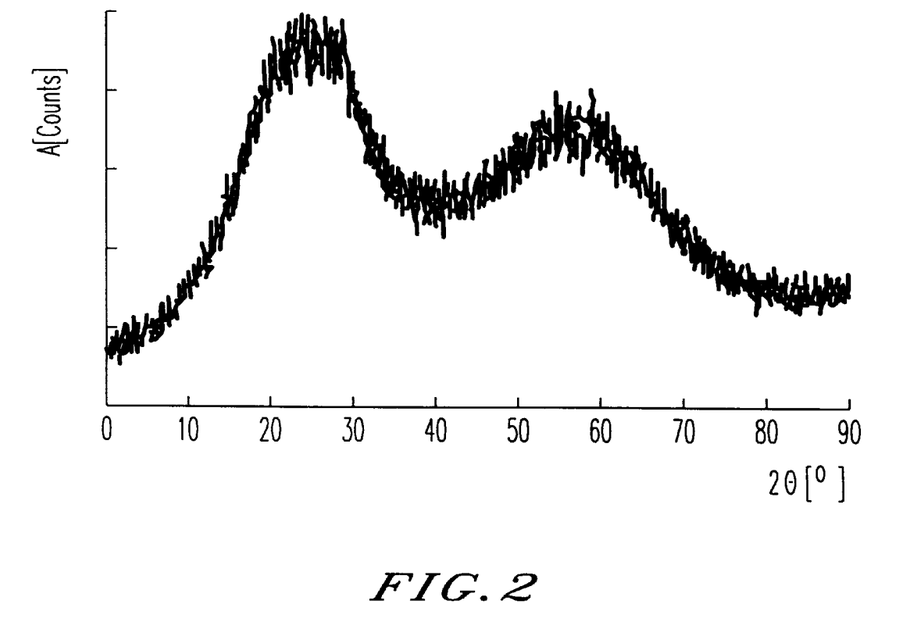

The essentially X-ray amorphous zinc silicate thus obtainable contains $Zn^{2+}$, $Si^{4+}$ and $O^{2-}$ ions; in addition, the compound may contain OH ions and water of hydration. The Zn/Si-ratio is from 0.3 to 5, preferably from 1 to 2.7, particularly preferably 2 to 2.3, very particularly preferably 2. In the last-mentioned case, the X-ray amorphous zinc silicate thus has the Zn/Si ratio of the crystalline hemimorphite $(Zn_4Si_2O_7(OH)_2.H_2O)$. The powder X-ray diffraction pattern of the novel X-ray amorphous zinc silicate, obtained using Cu-K$\alpha_1$ radiation ($\lambda$=1.5406 Å), is shown in FIG. 2, the intensity A of the diffracted X-rays having been plotted as a function of twice the diffraction angle (2θ). In the 2θ-range from 10° to 90°, the powder X-ray diffraction pattern of the X-ray amorphous zinc silicate to be used according to the invention has very broad intensity maxima at 2θ=31°±5° and at 2θ=61°±7°. Over and above the stated broad reflections of the X-ray amorphous zinc silicate to be used according to the invention, FIG. 2 shows further relatively sharp lines which can be associated with the formation of small amounts of crystalline ZnO (index card 5-0664 of the JCPDS-ICDD-index (1995)). In addition, small amounts of $Zn_5(NO_3)_2(OH)_8.2\ H_2O$ may also occur (index card 24-1460 of the JCPDS-ICDD index (1995)).

Furthermore, the amorphous zinc silicate precipitated catalyst to be used according to the invention can be doped with up to 80, preferably up to 50, in particular up to 20, mol percent of further metals selected from the group (A) consisting of beryllium, magnesium, calcium, strontium, barium, manganese, iron, cobalt, nickel, copper, cadmium and mercury and from the group (B) consisting of titanium, zirconium, hafnium, germanium, tin and lead, the elements of group (A) partially replacing zinc and the elements of group (B) partially replacing silicon in the hemimorphite structure.

The novel X-ray amorphous zinc silicate is obtained in the preparation as powder. This powder may be used as such for the catalytic reaction (for example in a fluidized-bed reactor) or after molding (for example extrusion, pelleting, etc., if necessary also with the addition of assistants) in a form suitable for a fixed-bed reactor.

Before use, the catalyst may be calcined from 800° C. to 750° C. The catalyst is preferably calcined at from 120° C. to 500° C. Calcination at from 200° to 400° C. in the air is particularly preferred. To increase the pore volume, pore formers (for example superabsorbers such as Lutexal P® (from BASF AG) or Walocel® (methylcellulose/synthetic resin combination, from Wolff, Walsrode AG)) may also be added during the shaping, for example during pelleting or extrusion.

(A) General reaction conditions

Figure 1:
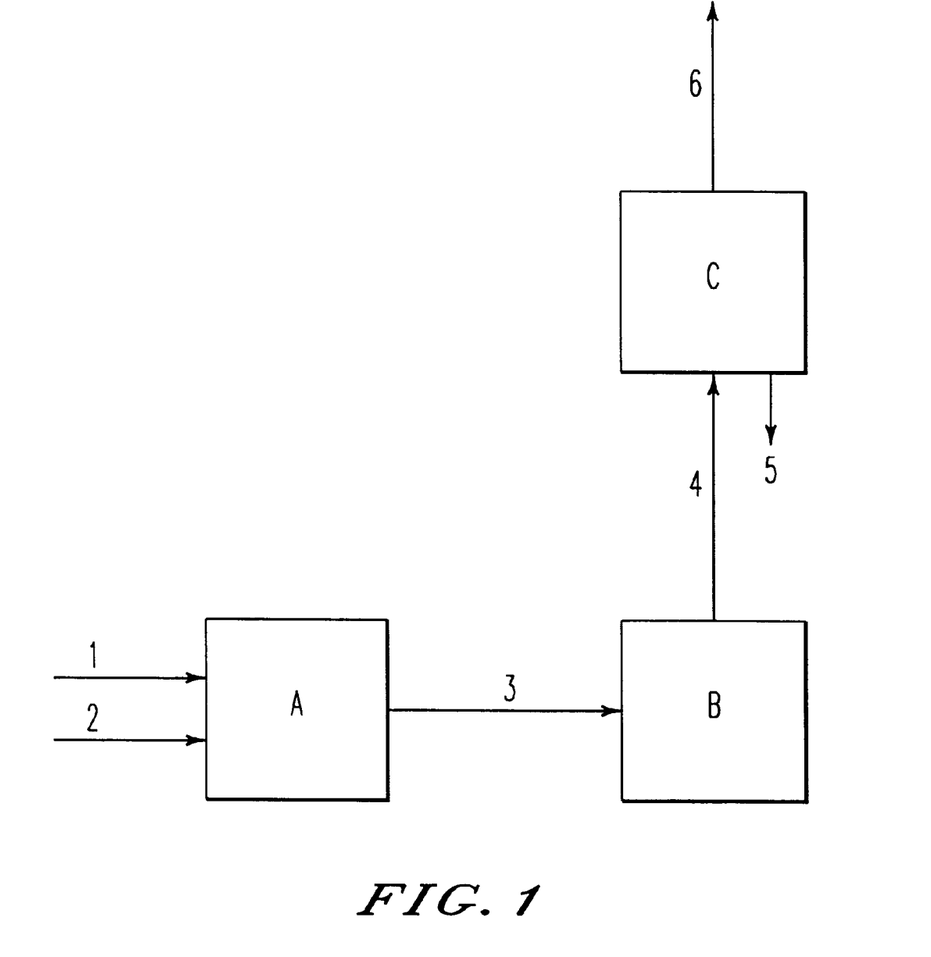

The catalytic reactions according to FIG. 1 were carried out in a gradient-free CSTR (continuously stirred tank reactor) (A) having a volume of 1740 ml and a catalyst volume of about 90 ml, modified for heterogeneous gas-phase reactions. The reactor had an internal diameter of about 108 mm and a height of about 200 mm and was heated by means of an electrical heating coil mounted on the inner surface. A small metal cylinder (Ø about 64 mm, height about 150 mm) was mounted in the middle of the reactor, and was provided at half height (about 85 mm below the upper eg.) with a wire grid. The catalyst was loosely poured onto this wire grid. A flat (Ø about 100 mm, height about 20 mm) turbine driven at 1500–2000 rpm as mounted on the reactor cover. A total of 6 thermocouples for temperature monitoring were mounted at various heights along the reactor axis. The starting materials were metered under pressure by means of HPLC pumps, mixed shortly before the reactor and let down into the reactor space. The alkyne and allene (1 in FIG. 1) were metered in either in pure form or as a mixture diluted with other inert components. In the case of propyne and allene, a mixture with other hydrocarbons was used (composition: 30–43% by volume of propyne, 16–20% by volume of allene, 20–45% by volume of propene, 5–10% by volume of isobutane and 2–6% by volume of propane as main components; all other components less than 1%). This mixture was obtained by distillation from a sidestream of a steam cracker. About 10% by weight of cyclohexane as an internal standard for the GC analysis were metered into the ketal (2 in FIG. 1).

The reaction was carried out isothermally at from 120 to 300° C. and at a feed rate of from 0.5 to 10 mmol/min of propyne and/or allene and from 0.5 to 20 mmol/min of ketal. The reaction pressure was from 1.1 to 3.5 bar (absolute).

The total amount, consisting of starting materials, inert gas and internal standard, was, as a rule, from 4 to 60 l(s.t.p.)/h. The GHSV (gas hourly space velocity), which is defined as GHSV=gas volume [l(s.t.p.)/h]/catalyst volume [l], was from 80 to 1200 h$^{-1}$. The LHSV (liquid hourly space velocity), which is defined as LHSV=liquid volume [l(s.t.p.)/h]/catalyst volume [l] (in this case the transported volume of propyne and volume of methanol), was from 0.2 to 3 h$^{-1}$. The residence time, defined as the quotient of the catalyst volume [l] and the amount of gas [l(s.t.p.)/s], was from 3 to 40 s.

After leaving the reactor, the reaction gases were passed via a heated transfer line (3) to an on-line gas chromatograph (B) and analyzed there every 2 hours. Thereafter, the gas stream was subjected to a partial condensation (C) and the fraction (6) which was not condensable at room temperature was analyzed at regular intervals (about 12 hours) by means of off-line GC. The condensate (5) was likewise collected and was analyzed by means of off-line GC.

Unless stated otherwise, the conversions and selectivities were based on the sum of propyne and allene.

EXAMPLE 1 a) Catalyst preparation (amorphous zinc silicate; by impregnation)

The Zn/SiO$_2$ supported catalyst was obtained by impregnating X-ray amorphous SiO$_2$ moldings (beads of Ø 3–6 mm) having a BET surface area of 358 m$^2$/g, a water absorptivity of 0.9 ml/g and a hardness of 43 N/molding with ammoniacal zinc acetate solution. For this purpose, 225 g of SiO$_2$ carrier (Siligel, from Solvay) were impregnated with 151.70 g of Zn(OAc)$_2$.2 H$_2$O (Merck), dissolved in 220 g of 9% strength NH$_4$OH solution at room temperature, and the precatalyst was then dried for 16 hours at 120° C. and then calcined for 4 hours at 250° C. under air. The precatalyst had a BET surface area of 195 m$^2$/g and a hardness of 76 N/molding. The acetate/Zn ratio was 0.9 mol/mol.

b) Reaction

About 90 ml of the precatalyst were introduced into the apparatus described in relation to FIG. 1. Propyne/allene mixture (55 mol %, remainder propene) and 2,2-dimethoxypropane were then metered in by means of HPLC pumps. The reaction was continued at the first setting (170° C.) until the active catalyst had completely formed and the conversion and selectivity were constant (about 12 hours). The temperature and the feeds were then changed according to Table 1. The results are summarized in Table 1. The pressure in all the experiments was 1.35 bar (absolute). Abbreviations: 2 MP: 2-methoxypropene; 22 DMP: 2,2-dimethoxypropane; 1 MP: 1-methoxypropene (cis and trans); 11 DMP: 1,1-dimethoxypropane. The selectivities stated are based on propyne and allene.

TABLE 1

| Experiment No. | Temp. ° C. | Feeds/mmol/min | | Conversions/% | | | Selectivities/% | | | |
|---|---|---|---|---|---|---|---|---|---|---|
| | | Propyne/Allene | 22 DMP | Total | Propyne/Allene | 22 DMP | 2 MP | Acetone | 1 MP | 11 DMP |
| 1.1 | 170 | 2.31 | 2.17 | 6.20 | 69 | 90 | 95 | 1 | 2 | <1 |
| 1.2 | 150 | 1.36 | 1.57 | 4.26 | 57 | 69 | 96 | 1 | 2 | <1 |
| 1.3 | 130 | 1.13 | 1.11 | 3.31 | 44 | 59 | 96 | 1 | 2 | <1 |

A BET surface area of 220 m$^2$/g and a hardness of 74 N/molding were determined for the catalyst removed from the reactor after the end of the test series.

EXAMPLE 2 a) Catalyst preparation (amorphous zinc silicate, Na-doped)

The Zn/SiO$_2$ supported catalyst was obtained by impregnating X-ray amorphous SiO$_2$ moldings (Siliperl AF125, from Engelhard, beads of Ø 3–6 mm having a BET surface area of 413 m$^2$/g, water absorptivity of 0.99 ml/g and a hardness of 29 N/molding) with ammoniacal zinc acetate solution. For this purpose, an impregnation solution consisting of 131.46 g of Zn(OAc)$_2$.2 H$_2$O (Merck) and 2.08 g of Na(OAc).3 H$_2$O dissolved in a mixture of 160 g of distilled water and 120 g of 25% strength NH$_4$OH solution was divided into two parts with 195 ml each and 200 g of SiO$_2$ carrier were impregnated at room temperature with the first part, the precatalyst was then dried for 16 hours at 120° C., impregnated with the second part at room temperature, then dried for 16 hours at 120° C. and then calcined at 250° C. for 4 hours under air.

The precatalyst had a BET surface area of 215 m$^2$/g and a hardness of 42 N/molding and was composed of 19.5% of ZnO, 0.5% of Na$_2$O and 80% of SiO$_2$.

b) Reaction

About 90 ml of the precatalyst were introduced into the apparatus described in relation to FIG. 1. Propyne/allene mixture (59 mol %, remainder propene) and 2,2-dimethoxypropane were then metered in by means of HPLC pumps. The reaction was continued at the first setting (175° C.) until the active catalyst had completely formed and the conversion and selectivity were constant (about 12 hours). The temperature and the feeds were then changed according to Table 2. The results are summarized in Table 2.

The pressure in all the experiments was 1.3 bar (absolute). Abbreviations: 2 MP: 2-methoxypropene; 22 DMP: 2,2-dimethoxypropane; 1 MP: 1-methoxypropene (cis and trans); 11 DMP: 1,1-dimethoxypropane. The selectivities stated are based on the sum of propyne and allene.

The dried white powder was investigated by X-ray diffraction, resulting in a powder X-ray diffraction pattern which fully corresponded to that of index card 5-0555 of the JCPDS-ICDD index (1995) and hence indicated the preparation of Zn$_4$Si$_2$O$_7$(OH)$_2$.H$_2$O. The specific surface area of the resulting powder, determined according to BET, was 30 m$^2$/g.

For the preparation of a catalyst, the still moist powder was directly milled to give extrudates (Ø=3 mm, extrusion pressure=50 bar), which were then dried for 16 hours at 120° C. The prepared catalyst had a BET surface area of 26 m$^2$/g and a hardness of 6 N/molding.

b) Reaction

About 90 ml of the catalyst were introduced into the apparatus described above. Propyne/allene mixture (about 63% by volume, 1.68 mmol/min) and 2,2-dimethoxypropane (2.17 mmol/min; total feed with inert substances: 6.46 mmol/min; 2,2-dimethoxypropane/(propyne+allene) ratio=1.29) were then metered in by means of HPLC pumps. The reaction temperature was 170° C. and the pressure was 1.35 bar (absolute) and the partial pressure of the starting materials was 0.8 bar. The following selectivities were observed from the beginning (ie. the catalyst had no forming time): 2-methoxypropene: 97.4%; acetone: 2.3%; cis- and trans-1-methoxypropene: 0.3%.

TABLE 2

| Experiment No. | Temp. ° C. | Feeds/mmol/min | | | Conversions/% | | Selectivities/% | | | |
|---|---|---|---|---|---|---|---|---|---|---|
| | | Propyne/Allene | 22 DMP | Total | Propyne/Allene | 22 DMP | 2 MP | Acetone | 1 MP | 11 DMP |
| 2.1 | 175 | 0.90 | 1.18 | 5.52 | 85 | 88 | 95 | 2 | 2 | <1 |
| 2.2 | 160 | 2.13 | 2.51 | 12.09 | 68 | 78 | 96 | 2 | 2 | <1 |
| 2.3 | 150 | 2.13 | 2.48 | 12.01 | 58 | 63 | 96 | 2 | 1 | <1 |
| 2.4 | 135 | 1.24 | 1.21 | 6.19 | 42 | 47 | 96 | 2 | 1 | <1 |
| 2.5 | 120 | 2.00 | 2.50 | 11.84 | 35 | 29 | 96 | 3 | 1 | <1 |

A BET surface area of 213 m$^2$/g and a hardness of 45 N/molding were determined for the catalyst removed from the reactor after the end of the test series.

EXAMPLE 3 a) Catalyst preparation (hemimorphite Zn/Si=2)

In an 8 l stirred container, a suspension A containing 1.5 mol of SiO$_2$ and 0.89 mol of Na was prepared from 4.5 l of demineralized water and 145.1 g of soda waterglass powder having an SiO$_2$ content of 62.1% by weight and an Na$_2$O content of 19.0% by weight (from Riedel-de Haen, D-30918 Seelze). Furthermore 910.7 g of Zn(NO$_3$)$_2$.6 H$_2$O (98% strength) were dissolved in 2.25 l of demineralized water at room temperature, a solution B containing 3 mol of Zn and 6 mol of NO$_3$ being obtained. Finally, an aqueous solution of 204.4 g of NaOH in 0.225 l of demineralized water was prepared, A solution C having an Na content of 5.11 mol being obtained. The solutions B and C were then added to the suspension A at room temperature, a milky suspension D having the following elemental contents being obtained: Zn content=3 mol, Si content=1.5 mol, Na content=6 mol, NO$_3$ content=6 mol. The pH of the resulting suspension D was 7.1. The suspension D was heated to 90° C. and was stirred at a speed of 200 rpm for 24 hours at this temperature. The suspension was then cooled to room temperature, and a final pH of 7.0 was measured. The white precipitate which had crystallized out was filtered off and washed Na-free with demineralized water, and the resulting filter cake was dried at 90° C. in a drying oven.

The following values were determined for the catalyst after removal from the reactor: BET 25 m$^2$/g, hardness 6 N/molding.

EXAMPLE 4 a) Catalyst preparation (hemimorphite Zn/Si=2.2)

In a 6 l stirred container, a suspension A containing 1.0 mol of SiO$_2$ and 0.59 mol of Na was prepared from 3.0 l of demineralized water and 96.8 g of soda waterglass powder having an SiO$_2$ content of 62.1% by weight and an Na$_2$O content of 19.0% by weight (from Riedel-de Haen, D-30918 Seelze), and a solution B containing 2.2 mol of Zn and 4.4 mol of NO$_3$ was prepared from 667.8 g of Zn(NO$_3$)$_2$.6 H$_2$O (98% strength) in 1.5 l of demineralized water at room temperature, and an aqueous solution C having an Na content of 3.81 mol was prepared from 152.3 g of NaOH in 0.4 l of demineralized water. The solutions B and C were added to the suspension A at room temperature, a milky suspension D having the following elemental contents being obtained: Zn content=2.2 mol, Si content=1 mol, Na content=4.4 mol, NO$_3$ content=4.4 mol. The pH of the resulting suspension D was 7.2. The suspension D was heated to 90° C. and stirred at a speed of 200 rpm for 24 hours at this temperature. After the suspension had cooled to room temperature, a final pH of 7.0 was measured. The resulting white precipitate was filtered off and washed Na-free with demineralized water and the resulting filter cake was dried at 90° C. in a drying oven. The dried white powder was investigated by X-ray diffraction, resulting in a powder X-ray diffraction pattern which fully corresponded to that of index card 5-0664 of the JCPDS-ICDD index (1995) and hence indicated the preparation of $Zn_4Si_2O_7(OH)_2 \cdot H_2O$. The specific surface area of the resulting powder, determined according to BET, was 60 $m^2/g$.

650 g of the powder were mixed with 20.2 g of magnesium stearate (Merck) and pressed to give 20 mm pellets. These pellets were processed to chips (<0.5 mm). The pellets were then calcined for 10 hours at 350° C. The prepared catalyst had a BET surface area of 44 $m^2/g$ and a hardness of 44 N/molding.

b) Reaction

About 90 ml of the catalyst were introduced into the apparatus described above. Propyne/allene mixture (about 60% by volume, 1.64 mmol/min) and 2,2-dimethoxypropane (2.14 mmol/min; total feed with inert substances: 8.34 mmol/min; 2,2-dimethoxypropane/(propyne+allene) ratio=1.30) were then metered in by means of HPLC pumps. The reaction temperature was 170° C. and the pressure was 1.35 bar (absolute) and the partial pressure of the starting materials was 0.8 bar. The following selectivities were observed from the beginning (ie. the catalyst had no forming time): 2-methoxypropene: 97.0%; acetone: 2.3%; cis- and trans-1-methoxypropene: 0.5%.

The following values were determined for the catalyst after removal from the reactor: BET 44 $m^2/g$, hardness 12 N/molding.

EXAMPLE 5

(X-ray amorphous precipitated catalyst; Zn/Si ratio 2.1)

In a 12 l stirred container, 120.93 g of soda waterglass powder having an $SiO_2$ content of 62.1% by weight and an $Na_2O$ content of 19.0% by weight (from Riedel-de-Haen, D-30918 Seelze) were added to 7.5 l of demineralized water at 80° C. with continuous stirring (100 rpm), a suspension A containing 1.25 mol of $SiO_2$ and 0.74 mol of Na being obtained. An aqueous solution B of 180.4 g of NaOH (equivalent to 4.51 mol of Na) in 0.5 l of demineralized water was then prepared. In addition, 796.8 g of $Zn(NO_3)_2 \cdot 6H_2O$ (Zn content=98%) were dissolved in 2.5 l of demineralized water, a solution C containing 2.625 mol of Zn and 5.25 mol of $NO_3$ being obtained. The solution B was then added to the suspension A at 80° C., a clear solution D being obtained after about 5 minutes. The solution C was then added to the resulting solution D. A white suspension E having a Zn content of 2.625 mol, an Si content of 1.25 mol, an Na content of 5.25 mol and an $NO_3$ content of 5.25 mol resulted. The suspension E was heated at 80° C. for 2 hours with stirring (100 rpm) and then cooled to room temperature. After cooling, a final pH of 6.5 was measured. The resulting white precipitate was filtered off and washed Na-free with demineralized water. The resulting filter cake was dried at 80° C. in a drying oven.

The dried white powder was investigated by X-ray diffraction, resulting in a powder X-ray diffraction pattern which corresponds to that of FIG. 2 and hence indicated the preparation of predominant amounts of X-ray amorphous zinc silicate in addition to a small amount of crystalline ZnO (index card 5-0555 of the JCPDS-ICDD index (1995)). The specific surface area of the resulting powder, determined according to BET, was 102.1 $m^2/g$.

650 g of the amorphous zinc silicate prepared as described above having the composition of hemimorphite were mixed with 20.2 g of zinc stearate and precompacted to 20 mm pellets, then comminuted to chips having a diameter of <0.5 mm and then molded to give pellets measuring 4.75×5.2 mm. The catalyst had a BET surface area of 75 $m^2/g$ and a hardness of 43 N/pellet. A 100 g portion of the catalyst was then calcined at 350° C. for 10 hours in the air.

About 90 ml of the catalyst were introduced into the apparatus described above. Propyne/allene mixture (49.8% by volume, 1.84 mmol/min) and 2,2-dimethoxypropane (2.15 mmol/min; total feed with inert substances: 6.79 mmol/min; 2,2-dimethoxypropane/(propyne+allene) ratio= 1.17) were then metered in by means of HPLC pumps. The reaction temperature was 170° C. and the pressure was 1.35 bar (absolute) and the partial pressure of the starting materials was 0.8 bar. The following selectivities were observed: 2-methoxypropene 97.1%; 2-dimethoxypropane 2.5%, cis- and trans-1-methoxypropene 0.4%. The conversion, based on propyne/propadiene, was 21%.

This catalyst had virtually no forming time. The stated conversion and the selectivity were virtually constant from the beginning. The BET surface area was 82 $m^2/g$ after calcination and 64 $m^2/g$ after removal from the reactor. The hardness was 28 N/pellet after calcination and 36/N pellet after removal from the reactor.

We claim:

1. A process for the preparation of enol ethers of the formula I wherein $R^1$ is an aliphatic, cycloaliphatic, araliphatic, aromatic or heterocyclic radical which may carry further substituents which do not react with acetylenes or allenes, and the radicals R, independently of one another, are hydrogen or aliphatic, cycloaliphatic, araliphatic, aromatic or heterocyclic radicals, which may be bonded to one another to form a ring, and m is 0 or 1, wherein an acetal or ketal of the formula II is reacted with an acetylene or allene of the formula III or IV

III      IV

III

IV where R and $R^1$ have the abovementioned meanings, in the gas phase at a temperature from 50 to 400° C. in the presence of a heterogeneous catalyst selected from the group consisting of a zinc- silicon- and oxygen-containing heterogeneous catalyst and a cadmium- silicon- and oxygen-containing heterogeneous catalyst.

2. A process as claimed in claim 1, wherein the reaction is carried out in the presence of a catalyst which has a BET surface area of from 10 to 800 $m^2/g$.

3. A process as claimed in claim 1, wherein the catalyst used is an X-ray amorphous zinc silicate obtainable by applying a zinc salt to amorphous silica and forming the catalyst at from 50 to 400° C.

4. A process as claimed in claim 1, wherein a zinc silicate having the hemimorphite structure of formula $Zn_4Si_2O_7(OH)_{2-2y}O_y \cdot xH_2O$ where x and y are each from 0 to 1, is used.

5. A process as claimed in claim 1, wherein the catalyst used is an essentially X-ray amorphous zinc silicate obtainable by precipitation in aqueous solution and of the formula V $$Zn_aSi_cO_{-2c-0.5e}(OH)_e \cdot f\,H_2O \qquad V,$$

where e is from 0 to 2a+4c and the ratio a/c is from 1 to 3.5 and the ratio f/a is from 0 to 200.

6. The process as claimed in claim 1, wherein a ketal or acetal of the formula II is reacted with an acetylene or allene of the formula III or IV such that 2 mol of the same enol ether I are obtained.

7. A process as claimed in claim 1, wherein 2-methoxypropene is prepared by reacting 2,2-dimethoxypropane with methylacetylene and/or allene.

8. A process as claimed in claim 1, wherein the reaction is carried out at from 50 to 400° C. and from 0.1 to 50 bar.

* * * * *

UNITED STATES PATENT AND TRADEMARK OFFICE
CERTIFICATE OF CORRECTION

PATENT NO. : 6,211,416 B1
DATED : April 3, 2001
INVENTOR(S) : Teles et al.

Page 1 of 1

It is certified that error appears in the above-identified patent and that said Letters Patent is hereby corrected as shown below:

Title page,
Item [22], [86] and [87], the PCT information has been omitted. These items should read as follows:

Item [22] PCT filed: Jun. 10, 1998
Item [86] PCT No:. PCT/EP98/03521

§ 371 Date: Dec. 6, 1999
§ 102 (e) Date: Dec. 6, 1999

Item [87] PCT Pub. No.: WO98/58894
PCT Pub. Date: Dec. 30, 1998

Signed and Sealed this

Sixth Day of November, 2001

Attest:

NICHOLAS P. GODICI
*Attesting Officer*   *Acting Director of the United States Patent and Trademark Office*